United States Patent
Wachtel et al.

(10) Patent No.: US 8,602,024 B2
(45) Date of Patent: Dec. 10, 2013

(54) MEDICAMENTS MAGAZINE, AND A DEVICE AND METHOD FOR OPENING IT; MULTI-DOSE POWDER INHALER

(75) Inventors: Herbert Wachtel, Ingelheim am Rhein (DE); Johannes Geser, Ingelheim am Rhein (DE); Burkhard Metzger, Ingelheim am Rhein (DE); Michael Spallek, Ingelheim am Rhein (DE); Michael Krueger, Ingelheim am Rhein (DE); Herbert Kunze, Dortmund (DE); Achim Moser, Chemnitz (DE); Elmar Mock, Colombier (CH); Antonino Lanci, Bern (CH); Andre Klopfenstein, La Neuveville (CH)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1381 days.

(21) Appl. No.: 12/296,984

(22) PCT Filed: Apr. 13, 2007

(86) PCT No.: PCT/CH2007/000178
§ 371 (c)(1),
(2), (4) Date: Dec. 30, 2008

(87) PCT Pub. No.: WO2007/118340
PCT Pub. Date: Oct. 25, 2007

(65) Prior Publication Data
US 2009/0101145 A1    Apr. 23, 2009

(30) Foreign Application Priority Data

Apr. 13, 2006   (EP) .................................. 06405161

(51) Int. Cl.
*A61M 15/00*   (2006.01)
*A61M 16/00*   (2006.01)
*B05D 7/14*    (2006.01)
*B65D 83/04*   (2006.01)
*B65D 83/06*   (2006.01)
*B65D 85/02*   (2006.01)

(52) U.S. Cl.
USPC ................. 128/203.15; 128/203.21; 206/538; 206/820

(58) Field of Classification Search
USPC ............. 128/203.15, 203.21, 203.12; 221/22; 220/507, 523–524; 206/484, 538–539, 206/820
See application file for complete search history.

(56) References Cited

U.S. PATENT DOCUMENTS 3,482,733 A * 12/1969 Groves ............................ 221/25
4,884,719 A * 12/1989 Levine et al. ................... 221/25

(Continued)

FOREIGN PATENT DOCUMENTS

| DE | 198 35 940 A1 | 2/2000 |
| EP | 1 003 478 B1 | 5/2000 |
| WO | 2004/067069 A1 | 8/2004 |

*Primary Examiner* — Jackie Ho
*Assistant Examiner* — Mark K Han
(74) *Attorney, Agent, or Firm* — Michael P. Morris; Wendy A. Petka

(57) ABSTRACT

The invention relates to a medicament magazine with a plurality of doses of medicament, wherein the magazine is formed from a single foil strip in which pouches (2) for holding a medicament are formed as depicted in exemplary FIG. 1. The foil strip comprises for transporting the strip openings (4) on at least one side for the engagement of transporting pins. The foil strip has a certain width in the region of the pouches, which is less than the width of the foil in other regions, and the openings are arranged in this broader part of the foil strip. The invention also relates to a method and a device for opening a medicament magazine of this kind, the device preferably being constructed as a segmented wheel.

19 Claims, 4 Drawing Sheets

(56) References Cited

U.S. PATENT DOCUMENTS

| | | | |
|---|---|---|---|
| 5,207,217 A * | 5/1993 | Cocozza et al. | 128/203.21 |
| 5,497,763 A | 3/1996 | Lloyd et al. | |
| 5,823,178 A * | 10/1998 | Lloyd et al. | 128/200.14 |
| 6,082,356 A * | 7/2000 | Stradella | 128/203.15 |
| 6,929,004 B1 | 8/2005 | Bonney et al. | |
| 7,278,424 B1 * | 10/2007 | Davies et al. | 128/203.15 |
| 8,443,798 B2 * | 5/2013 | Eason et al. | 128/203.12 |
| 8,474,453 B2 * | 7/2013 | Eason et al. | 128/203.15 |
| 2005/0172962 A1 | 8/2005 | Gumaste et al. | |
| 2005/0237222 A1 * | 10/2005 | Bogash et al. | 340/870.07 |

* cited by examiner

MEDICAMENTS MAGAZINE, AND A DEVICE AND METHOD FOR OPENING IT; MULTI-DOSE POWDER INHALER

This application is the national phase entry under 35 U.S.C. §371 of International Application No. PCT/CH2007/000178, filed Apr. 13, 2007, which claims priority to European Application No. EP 06405161.8, filed Apr. 13, 2006, each of which is hereby incorporated by reference in its entirety.

BACKGROUND OF THE INVENTION

The invention relates to the field of medicament magazines, particularly medicament magazines in which pouches for holding a medicament are formed in a single film strip, according to the preamble of the independent claim. The invention also relates to a device and a method for opening the medicament magazine, and a multi-dose powder inhaler.

From the publication US 2005/0172962 a foil blister is known in which a single foil band is folded into individual medicament pouches. The band has openings along its length on one side. A sprocket wheel engages in these openings, blocking the blister in position as soon as a medicament pouch has reached a piezoelectric element. A winding reel on the opposite side of the piezoelectric element winds up the foil band. The reel continues to pull in the foil until the corresponding medicament pouch has been opened and the medicament contained therein can be shaken out of the foil by means of the piezoelectric element. This blister and opening mechanism has a number of disadvantages. On the one hand, the blister band including pouch has to roll over the sprocket. To do this, openings in the pouches and the rest of the band have to register precisely so as not to be "lifted" off the sprocket. This also casts doubt on the reliable engagement of the wheel in the blister after the pouch has gone through. In addition, the individual pouches have to be spaced apart by more than a pouch length so as not to lie on the sprocket. However, this restricts the desired high density of pouches arranged behind one another. Moreover, the opening mechanism described takes up a lot of space on account of the wide-apart arrangement of the wheels.

The specifications DE 198 35 940 and WO 2004/067069 disclose medicament magazines which have transporting openings or depressions on both sides in the edge regions of the strip-shaped magazine. These magazines are constructed as foil blisters, however, in which a covering foil is pressed through or peeled off. The disadvantages mentioned in US 2005/0172962 in relation to a single-foil folded blister are therefore not overcome in these specifications.

The aim of the invention is therefore to improve the known single-foil folded blisters and overcome the disadvantages described so as to provide a wider range of options in terms of the handling of the foil blister.

The invention solves the problem by means of the medicament magazine and the apparatus and process as defined in the independent claims.

Preferred embodiments of the invention are described in the sub-claims.

The medicament magazine according to the invention has a plurality of doses of medicament, the magazine being formed from a single foil strip in which are formed pouches for holding the doses of medicament. The foil strip has openings for the transporting of the strip on at least one side for the engagement of transporting pins. At the same time the foil strip has a certain width in the region of the pouches which is less than the width of the foil in other areas, the openings being arranged in this wider part of the foil strip.

The advantage of this is that the foil blister can be guided laterally substantially independently of the position, lie and mass of the individual pouches. The pouches can be arranged above one another in a space-saving manner, e.g. like scales, without affecting the transporting of the strip. Also, transporting and opening means can immediately adjoin one another or be combined in a single element. The pouches may be arranged directly adjacent to a transporting and/or opening means, e.g. in a space between two parallel wheels. A foil blister and a device in which such a foil blister is accommodated can thus be designed to be very compact.

After fabrication to make a medicament magazine a foil strip has at least one pouch in which a medicament, for example a powder, is accommodated. In front of or behind the at least one pouch, or, in the case of a plurality of pouches, between them, the foil band is wider and contains the openings for transporting the blister, preferably also for opening the blister. The broader part of the blister comprising the openings forms an edge along the magazine, which is preferably substantially the same width as the openings. However, as the openings are arranged only between the pouches, the width of the openings is not critical: no medicament chamber is damaged by the provision of openings, nor is the size of such a chamber affected by the size of the openings.

Preferably, there are openings in both edges of the foil strip. This allows very controlled, particularly symmetrical, transporting and optionally also opening of the magazine or of a pouch. In the region between the wheels, one or more pouches may hang or lie freely, independently of the guiding of the medicament magazine by the pins.

The arrangement and configuration of the openings can be used for transporting, stopping and opening a blister. However, it is also possible to use these for other functions, e.g. for indexing and/or monitoring. A distinction can be made between individual pouches for example by means of differences in size, e.g. length, or the spacings of openings. It is also possible thereby to control the indication of the doses of medicament which have been used or are yet to be used.

The medicament pouches may be formed symmetrically in the foil strip. However, it is also possible to provide one side of the pouch with a depression and then to make the cover as a substantially planar surface, or to first form a loop with the foil and then to close it by suitable sealing before or after filling.

A device for opening a medicament magazine comprises at least one movable pin for engaging in an opening provided for this purpose in the magazine. In addition, it comprises transporting means for a magazine and opening means for a magazine in order to open a pouch formed in a foil strip. The at least one pin is arranged such that it engages in the foil strip laterally, in relation to a direction of travel, at a spacing from the pouch. As a result of the different foil widths in the region of the pouches and between the pouches, the pin, or for example a sprocket wheel comprising a plurality of pins, is guided parallel and laterally with respect to the pouches. Because of this laterally spaced guiding of the pin and pouch parallel to the direction of travel, optionally directly adjacent to one another or slightly offset one behind the other, the pouch is substantially freely movable next to the pin. A transporting pin is preferably a tooth on a sprocket wheel, while in a preferred embodiment at least two pins are arranged parallel to one another and spaced apart from one another by the width of at least one medicament pouch, such that a pouch is substantially freely movable between the pins or a transporting and/or opening means that comprises the pins. A transporting movement and an opening movement are two individual steps carried out one after the other, according to a preferred embodiment.

In the device for opening a medicament magazine the transporting and opening means are preferably combined in a single means, which preferably takes the form of a discontinuous pin wheel, e.g. a segmented wheel.

During the transporting and opening of a medicament magazine at least one pin engages in an opening provided therefor in the medicament magazine which preferably has a plurality of medicament pouches and brings the magazine into an opening position by a transporting movement. The part of the magazine that is located in front of a medicament pouch in the region of an opening position is held in place and the part of the magazine which is located after this medicament pouch is conveyed onwards by means of the at least one pin. In this way the medicament pouch is pulled open, by freeing the areas of the foil that are attached to one another, and the medicament contained in the pouch is released, e.g. for inhalation.

A medicament pouch is preferably opened by at least two pins engaging in the medicament magazine and moving away relative to one another. If the pins are part of a segmented wheel the pins belong to different segments of the wheel and a medicament pouch is opened by moving these segments apart or opening them. A medicament chamber is arranged between the two segments of the segmented wheel.

In a preferred embodiment of the apparatus and the process, an opening movement and a transporting movement take place in the same direction. An opened medicament chamber is preferably also in the same plane as the medicament magazine during transportation into the opening position, but particularly in the same plane as the magazine with the pouch which is to be opened during the opening process.

The medicament magazine according to the invention and the opening device are typically used in a medicament dispensing device, preferably an inhaler, such as a multi-dose powder inhaler. The number of doses is preferably in the range from 1 to 100 or up to 200 single doses, preferably in the range from 1-60, for example between 7-180 or 14-150, e.g. 30-120, 45-100, 30, 90, 60, 120. For inhalers the maximum number of single doses is preferably 60, for reasons of convenience and therapy.

A multi-dose powder inhaler according to the invention thus comprises a medicament magazine according to the invention and/or a device according to the invention for opening such a magazine.

The pharmaceutically active substances, substance formulations or mixtures of substances used may be any inhalable compounds, such as e.g. inhalable macromolecules, as disclosed in EP 1 003 478. Preferably, substances, substance formulations or mixtures of substances which are taken by inhalation are used for treating respiratory complaints.

The compounds specified below may be used in the apparatus on their own or in combination. In the compounds specified below, W is a pharmacologically active substance and (for example) is selected from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors. Moreover, double or triple combinations of W may be combined and used in the apparatus accin. Combinations of W might be, for example:

W denotes a betamimetic, combined with an anticholinergic, corticosteroid, PDE4-inhibitor, EGFR-inhibitor or LTD4-antagonist, W denotes an anticholinergic, combined with a betamimetic, corticosteroid, PDE4-inhibitor, EGFR-inhibitor or LTD4-antagonist, W denotes a corticosteroid, combined with a PDE4-inhibitor, EGFR-inhibitor or LTD4-antagonist W denotes a PDE4-inhibitor, combined with an EGFR-inhibitor or LTD4-antagonist W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide 5-[2-(5,6-diethyl-indan-2-ylamino)-1-hydroxy-ethyl]-8-hydroxy-1H-quinoline-2-one 4-hydroxy-7-[2-{[2-{[3-(2-phenylethoxy)propyl] sulphonyl}ethyl]-amino}ethyl]-2(3H)-benzothiazolone 1-(2-fluoro-4-hydroxyphenyl)-2-[4-(1-benzimidazolyl)-2-methyl-2-butylamino]ethanol 1-[3-(4-methoxybenzyl-amino)-4-hydroxyphenyl]-2-[4-(1-benzimidazolyl)-2-methyl-2-butylamino]ethanol 1-[2H-5-hydroxy-3-oxo-4H-1,4-benzoxazin-8-yl]-2-[3-(4-N,N-dimethylaminophenyl)-2-methyl-2-propylamino] ethanol 1-[2H-5-hydroxy-3-oxo-4H-1,4-benzoxazin-8-yl]-2-[3-(4-methoxyphenyl)-2-methyl-2-propylamino]ethanol 1-[2H-5-hydroxy-3-oxo-4H-1,4-benzoxazin-8-yl]-2-[3-(4-n-butyloxyphenyl)-2-methyl-2-propylamino]ethanol 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol 5-hydroxy-8-(1-hydroxy-2-isopropylaminobutyl)-2H-1,4-benzoxazin-3-(4H)-on 1-(4-amino-3-chloro-5-trifluoromethylphenyl)-2-tert.-butylamino)ethanol 6-hydroxy-8-{1-hydroxy-2-[2-(4-methoxy-phenyl)-1,1-dimethyl-ethylamino]-ethyl}-4H-benzo[1,4]oxazin-3-one 6-hydroxy-8-{1-hydroxy-2-[2-(ethyl 4-phenoxy-acetate)-11-dimethyl-ethylamino]-ethyl}-4H-benzo[1,4]oxazin-3-one 6-hydroxy-8-{1-hydroxy-2-[2-(4-phenoxy-acetic acid)-1,1-dimethyl-ethylamino]-ethyl}-4H-benzo[1,4]oxazin-3-one 8-{2-[1,1-dimethyl-2-(2,4,6-trimethylphenyl)-ethylamino]-1-hydroxy-ethyl}-6-hydroxy-4H-benzo[1,4]oxazin-3-one 6-hydroxy-8-{1-hydroxy-2-[2-(4-hydroxy-phenyl)-1,1-dimethyl-ethylamino]-ethyl}-4H-benzo[1,4]oxazin-3-one 6-hydroxy-8-{1-hydroxy-2-[2-(4-isopropyl-phenyl)-1,1 dimethyl-ethylamino]-ethyl}-4H-benzo[1,4]oxazin-3-one 8-{2-[2-(4-ethyl-phenyl)-1,1-dimethyl-ethylamino]-1-hydroxy-ethyl}-6-hydroxy-4H-benzo[1,4]oxazin-3-one 8-{2-[2-(4-ethoxy-phenyl)-1,1-dimethyl-ethylamino]-1-hydroxy-ethyl}-6-hydroxy-4H-benzo[1,4]oxazin-3-one 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid 8-{2-[2-(3.4-difluoro-phenyl)-1,1-dimethyl-ethylamino]-1-hydroxy-ethyl}-6-hydroxy-4H-benzo[1,4]oxazin-3-one 1-(4-ethoxy-carbonylamino-3-cyano-5-fluorophenyl)-2-(tert-butylamino)ethanol 2-hydroxy-5-(1-hydroxy-2-{2-[4-(2-hydroxy-2-phenyl-ethylamino)-phenyl]-ethylamino}-ethyl)-benzaldehyde N-[2-hydroxy-5-(1-hydroxy-2-{2-[4-(2-hydroxy-2-phenyl-ethylamino)-phenyl]-ethylamino}-ethyl)-phenyl]-formamide 8-hydroxy-5-(1-hydroxy-2-{2-[4-(6-methoxy-biphenyl-3-ylamino)-phenyl]-ethylamino}-ethyl)-1H-quinolin-2-one 8-hydroxy-5-[1-hydroxy-2-(6-phenethylamino-hexylamino)-ethyl]-1H-quinolin-2-one 5-[2-(2-{4-[4-(2-amino-2-methyl-propoxy) -phenylamino]-phenyl}-ethylamino)-1-hydroxy-ethyl]-8-hydroxy-1H-quinolin-2-one

[3-(4-{6-[2-hydroxy-2-(4-hydroxy-3-hydroxymethyl-phenyl)-ethylamino]-hexyloxy}-butyl)-5-methyl-phenyl]-urea 4-(2-{6-[2-(2,6-dichloro-benzyloxy)-ethoxy]-hexylamino}-1-hydroxy-ethyl)-2-hydroxymethyl-phenol

[3-(4-{6-[2-hydroxy-2-(4-hydroxy-3-hydroxymethyl-phenyl)-ethylamino]-hexyloxy}-butyl)-benzylsulphonamide 3-(3-{7-[2-hydroxy-2-(4-hydroxy-3-hydroxymethyl-phenyl)-ethylamino]-heptyloxy}-propyl)-benzylsulphonamide 4-(2-{6-[4-(3-cyclopentanesulphonyl-phenyl)-butoxy]-hexylamino}-1-hydroxy-ethyl)-2-hydroxymethyl-phenol N-adamantan-2-yl-2-(3-{2-[2-hydroxy-2-(4-hydroxy-3-hydroxymethyl-phenyl)-ethylamino]-propyl}-phenyl)-acetamide, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

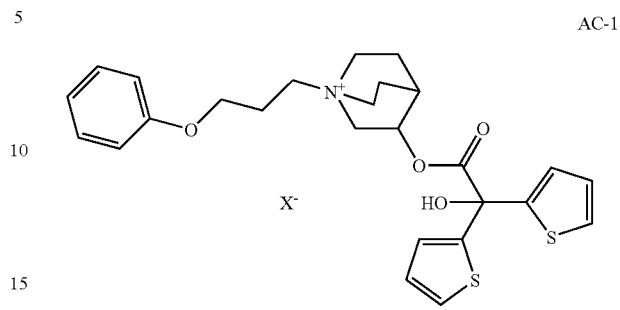

AC-1 wherein $X^-$ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-ene

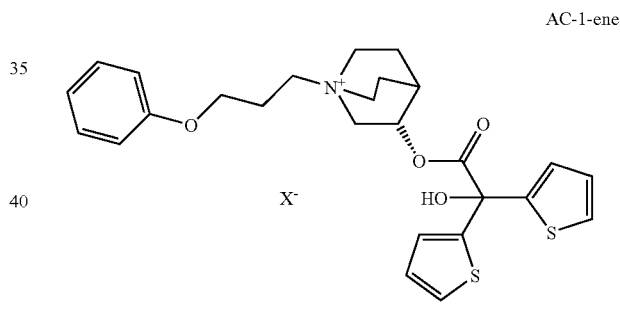

AC-1-ene wherein $X^-$ may have the above-mentioned meanings. Other preferred anticholinergics are selected from the salts of formula AC-2

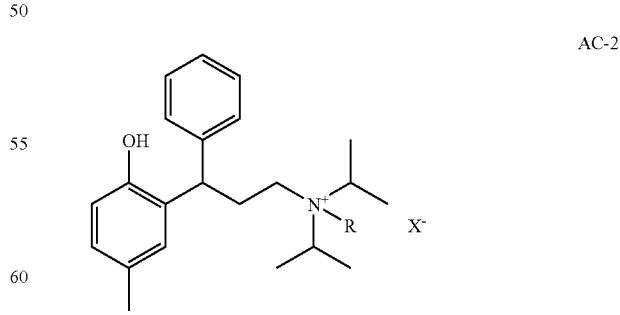

AC-2 wherein R denotes either methyl or ethyl and wherein $X^-$ may have the above-mentioned meanings. In an alternative embodiment the compound of formula AC-2 may also be present in the form of the free base AC-2-base.

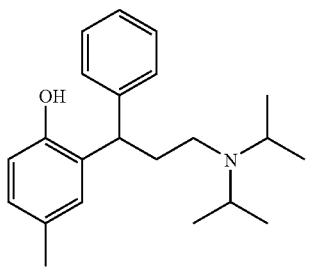

AC-2-base

Other specified compounds are:
tropenol 2,2-diphenylpropionate methobromide,
scopine 2,2-diphenylpropionate methobromide,
scopine 2-fluoro-2,2-diphenylacetate methobromide,
tropenol 2-fluoro-2,2-diphenylacetate methobromide;
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate-methobromide;
scopine 9-methyl-xanthene-9-carboxylate-methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide.

The above-mentioned compounds may also be used as salts within the scope of the present invention, wherein instead of the methobromide the salts metho-X are used, wherein X may have the meanings given hereinbefore for $X^-$.

As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and
(S)-fluoromethyl 6,9-difluoro-17-[(2-furanylcarbonyl)oxy]-11-hydroxy-16-methyl-3-oxo-androsta-1,4-diene-17-carbothionate
(S)-(2-oxo-tetrahydro-furan-3 S-yl)6,9-difluoro-1,1-hydroxy-16-methyl-3-oxo-17-propionyloxy-androsta-1,4-diene-17-carbothionate,
cyanomethyl 6α,9α-difluoro-11β-hydroxy-16α-methyl-3-oxo-17α-(2,2,3,3-tetramethylcyclopropylcarbonyl)oxy-androsta-1,4-diene-17β-carboxylate
optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325, 366, D-4396 (Sch-351591), AWD-12-281 (GW-842470), NCS-613, CDP-840, D-4418, PD-168787, T-440, T-2585, V-11294A, CI-1018, CDC-801, CDC-3052, D-22888, YM-58997, Z-15370 and
N-(3,5-dichloro-1-oxo-pyridin-4-yl)-4-difluoromethoxy-3-cyclopropylmethoxybenzamide
$(-)_p$-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide
(R)-(+)-1-(4-bromobenzyl)-4-[(3-cyclopentyloxy)-4-methoxyphenyl]-2-pyrrolidone
3-(cyclopentyloxy-4-methoxyphenyl)-1-(4-N'-[N-2-cyano-5-methyl-isothioureido]benzyl)-2-pyrrolidone
cis[4-cyano-4-(3-cyclopentyloxy-4-methoxyphenyl)cyclohexane-1-carboxylic acid]
2-carbomethoxy-4-cyano-4-(3-cyclopropylmethoxy-4-difluoromethoxy-phenyl)cyclohexan-1-one
cis[4-cyano-4-(3-cyclopropylmethoxy-4-difluoromethoxyphenyl)cyclohexan-1-ol]
(R)-(+)-ethyl[4-(3-cyclopentyloxy-4-methoxyphenyl)pyrrolidin-2-ylidene]acetate
(S)-(−)-ethyl[4-(3-cyclopentyloxy-4-methoxyphenyl)pyrrolidin-2-ylidene]acetate
9-cyclopentyl-5,6-dihydro-7-ethyl-3-(2-thienyl)-9H-pyrazolo[3,4-c]-1,2,4-triazolo[4,3-a]pyridine
9-cyclopentyl-5,6-dihydro-7-ethyl-3-(tert-butyl)-9H-pyrazolo[3,4-c]-1,2,4-triazolo[4,3-a]pyridine
optionally in the form of the racemates, enantiomers or diastereomers thereof and optionally in the form of the pharmacologically acceptable acid addition salts thereof, the solvates and/or hydrates thereof. According to the invention the acid addition salts of the PDE4 inhibitors are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3 (3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid

[2-[[2-(4-tert-butyl-2-thiazolyl)-5-benzofuranyl]oxymethyl]phenyl]acetic acid optionally in the form of the racemates, enantiomers or diastereomers thereof and optionally in the form of the pharmacologically acceptable acid addition salts, solvates and/or hydrates thereof. According to the invention these acid addition salts are preferably selected from among the hydrochloride, hydrobromide, hydroiodide, hydrosulphate, hydrophosphate, ydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]-amino}-7-cyclopropylmethoxy-quinazoline 4-[(3-chloro-4-fluorophenyl)amino]-6-{[4-(N,N-diethylamino)-1-oxo-2-buten-1-yl]amino}-7-cyclopropyl-methoxy-quinazoline 4-[(3-chloro-4-fluorophenyl)amino]-6-{[4-(N,N-dimethylamino)-1-oxo-2-buten-1-yl]amino}-7-cyclopropyl-methoxy-quinazoline 4-[(R)-(1-phenyl-ethyl)amino]-6-{[4-(morpholin-4-yl)-1-oxo-2-buten-1-yl]-amino}-7-cyclopentyloxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl) amino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxyethyl)-N-methyl-amino]-1-oxo-2-buten-1-yl} amino)-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethyl)amino]-6-{[4-(N,N-bis-(2-methoxyethyl)-amino)-1-oxo-2-buten-1-yl]amino}-7-cyclopropylmethoxy-quinazoline 4-[(R)-(1-phenyl-ethyl)amino]-6-({4-[N-(2-methoxyethyl)-N-ethyl-amino]-1-oxo-2-buten-1-yl} amino)-7-cyclopropylmethoxy-quinazoline 4-[(R)-(1-phenyl-ethyl)amino]-6-({4-[N-(2-methoxyethyl)-N-methyl-amino]-1-oxo-2-buten-1-yl} amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl} amino)-7-cyclopropylmethoxy-quinazoline 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline 4-[(3-chloro-4-fluorophenyl)amino]-6-({4-[N-(2-methoxyethyl)-N-methyl-amino]-1-oxo-2-buten-1-yl} amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline 4-[(3-ethynyl-phenyl)amino]-6.7-bis-(2-methoxy-ethoxy)-quinazoline 4-[(3-chloro-4-fluorophenyl)amino]-7-[3-(morpholin-4-yl)-propyloxy]-6-[(vinyl-carbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl)quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]-amino}-7-[(tetrahydrofuran-2-yl)methoxy]-quinazoline 4-[(3-chloro-4-fluorophenyl)amino]-6-({4-[N,N-bis-(2-methoxy-ethyl)-amino]-1-oxo-2-buten-1-yl} amino)-7-[(tetrahydrofuran-2-yl)methoxy]-quinazoline 4-[(3-ethynyl-phenyl)amino]-6-{[4-(5.5-dimethyl-2-oxo-morpholin-4-yl)-1-oxo-2-buten-1-yl]amino}-quinazoline 4-[(3-chloro-4-fluoro-phenyl)amino]-6-[2-(2.2-dimethyl-6-oxo-morpholin-4-yl)-ethoxy]-7-methoxy-quinazoline 4-[(3-chloro-4-fluoro-phenyl)amino]-6-[2-(2.2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2.2-dimethyl-6-oxo-morpholin-4-yl)-ethoxy]-6-[(S)-(tetrahydro furan-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(methoxymethyl)carbonyl]-piperidin-4-yloxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylaminoethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimethylamino)sulphonylamino]-cyclohexan-1-yloxy}-7-methoxy-quinazoline 4-[(3-chloro-4-fluoro-phenyl)amino]-6-{trans-4-[(morpholin-4-yl)carbonylamino]-cyclohexan-1-yloxy}-7-methoxy-quinazoline 4-[(3-chloro-4-fluoro-phenyl)amino]-6-{trans-4-[(morpholin-4-yl)sulphonylamino]-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[piperidin-1-yl]carbonyl]-piperidin-4-yloxy}-7-methoxy-quinazoline 4-[(3-chloro-4-fluoro-phenyl)amino]-6-(1-aminocarbonylmethyl-piperidin-4-yloxy)-7-methoxy-quinazoline 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline 4-[(3-chloro-4-fluoro-phenyl)amino]-6-(trans-4-ethansulphonylamino-cyclohexan-1-yloxy)-7-methoxy-quinazoline 4-[(3-chloro-4-fluoro-phenyl)amino]-6-(1-methanesulphonyl-piperidin-4-yloxy)-7-ethoxy-quinazoline 4-[(3-chloro-4-fluoro-phenyl)amino]-6-(1-methanesulphonyl-piperidin-4-yloxy)-7-(2-methoxy-ethoxy)-quinazoline 4-[(3-chloro-4-fluoro-phenyl)amino]-6-[1-(2-methoxy-acetyl)-piperidin-4-yloxy]-7-(2-methoxy-ethoxy)-quinazoline 4-[(3-chloro-4-fluoro-phenyl)amino]-6-(cis-4-acetylamino-cyclohexan-1-yloxy)-7-methoxy-quinazoline 4-[(3-ethynyl-phenyl)amino]-6-[1-(tert.-butyloxycarbonyl)-piperidin-4-yloxy]-7-methoxy-quinazoline 4-[(3-ethynyl-phenyl)amino]-6-(tetrahydropyran-4-yloxy]-7-methoxy-quinazoline 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline 4-[(3-chloro-4-fluoro-phenyl)amino]-6-{cis-4-[(morpholin-4-yl)carbonylamino]-cyclohexan-1-yloxy}-7-methoxy-quinazoline 4-[(3-chloro-4-fluoro-phenyl)amino]-6-{1-[2-(2-oxopyrrolidin-1-yl)ethyl]-piperidin-4-yloxy}-7-methoxy-quinazoline 4-[(3-chloro-4-fluoro-phenyl)amino]-6-{1-[(morpholin-4-yl)carbonyl]-piperidin-4-yloxy}-7-(2-methoxy-ethoxy)-quinazoline 4-[(3-ethynyl-phenyl)amino]-6-(1-acetyl-piperidin-4-yloxy)-7-methoxy-quinazoline 4-[(3-ethynyl-phenyl)amino]-6-(1-methyl-piperidin-4-yloxy)-7-methoxy-quinazoline 4-[(3-ethynyl-phenyl)amino]-6-(1-methanesulphonyl-piperidin-4-yloxy)-7-methoxy-quinazoline 4-[(3-chloro-4-fluoro-phenyl)amino]-6-(1-methyl-piperidin-4-yloxy)-7(2-methoxy-ethoxy)-quinazoline 4-[(3-chloro-4-fluoro-phenyl)amino]-6-(1-isopropyloxycarbonyl-piperidin-4-yloxy)-7-methoxy-quinazoline 4-[(3-chloro-4-fluoro-phenyl)amino]-6-(cis-4-methylamino-cyclohexan-1-yloxy)-7-methoxy-quinazoline 4-[(3-chloro-4-fluoro-phenyl)amino]-6-{cis-4-[N-(2-methoxy-acetyl)-N-methyl-amino]-cyclohexan-1-yloxy}-7-methoxy-quinazoline 4-[(3-ethynyl-phenyl)amino]-6-(piperidin-4-yloxy)-7-methoxy-quinazoline 4-[(3-ethynyl-phenyl)amino]-6-[1-(2-methoxy-acetyl)-piperidin-4-yloxy]-7-methoxy-quinazoline 4-[(3-ethynyl-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(cis-2,6-dimethyl-morpholin-4-yl)carbonyl]-piperidin-4-yloxy}-7-methoxy-quinazoline 4-[(3-chloro-4-fluoro-phenyl)amino]-6-{1-[(2-methyl-morpholin-4-yl)carbonyl]-piperidin-4-yloxy}-7-methoxy-quinazoline 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline 4-[(3-chloro-4-fluoro-phenyl)amino]-6-{1-[(N-methyl-N-2-methoxyethyl-amino)carbonyl]-piperidin-4-yloxy}-7-methoxy-quinazoline 4-[(3-chloro-4-fluoro-phenyl)amino]-6-(1-ethyl-piperidin-4-yloxy)-7-methoxy-quinazoline 4-[(3-chloro-4-fluoro-phenyl)amino]-6-{1-[(2-methoxyethyl)carbonyl]-piperidin-4-yloxy}-7-methoxy-quinazoline 4-[(3-chloro-4-fluoro-phenyl)amino]-6-{1-[(3-methoxypropyl-amino)-carbonyl]-piperidin-4-yloxy}-7-methoxy-quinazoline 4-[(3-chloro-4-fluoro-phenyl)amino]-6-[cis-4-(N-methanesulphonyl-N-methyl-amino)-cyclohexan-1-yloxy]-7-methoxy-quinazoline 4-[(3-chloro-4-fluoro-phenyl)amino]-6-[cis-4-(N-acetyl-N-methyl-amino)-cyclohexan-1-yloxy]-7-methoxy-quinazoline 4-[(3-chloro-4-fluoro-phenyl) amino]-6-(trans-4-methylamino-cyclohexan-1-yloxy)-7-methoxy-quinazoline 4-[(3-chloro-4-fluoro-phenyl) amino]-6-[trans-4-(N-methanesulphonyl-N-methyl-amino)-cyclohexan-1-yloxy]-7-methoxy-quinazoline 4-[(3-chloro-4-fluoro-phenyl)amino]-6-(trans-4-dimethylamino-cyclohexan-1-yloxy)-7-methoxy-quinazoline 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-[2-(2.2-dimethyl-6-oxo-morpholin-4-yl)-ethoxy]-7-[(S)-(tetrahydro furan-2-yl)methoxy]-quinazoline 4-[(3-chloro-4-fluoro-phenyl)amino]-6-(1-methanesulpho-nyl-piperidin-4-yloxy)-7-methoxy-quinazoline 4-[(3-chloro-4-fluoro-phenyl)amino]-6-(1-cyano-piperidin-4-yloxy)-7-methoxy-quinazoline optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorophenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Besides inhalable macromolecules may be used, as disclosed in EP 1 003 478.

In addition, the compound may from the group of the derivatives of ergot alkaloids, triptanes, CGRP-inhibitors, phosphodiesterase-V inhibitors, optionally in the form of the racemates, enantiomers or diastereomers thereof, optionally in the form of the pharmacologically acceptable acid addition salts, solvates and/or hydrates thereof.

Examples of ergot alkaloid derivatives are: dihydroergotamine, ergotamine.

Examples of substances suitable for inhalation include medicaments, medicament formulations and mixtures containing the above-mentioned active substances, and the salts and esters thereof and combinations of these active substances, salts and esters.

For producing medicament magazines, pharmaceutically permitted materials are preferably used. The films used for the single-foil folded blister may be multi-layer films, for example, which are also suitable for the production of conventional blisters. These are usually multi-layer films having a layer of PE, PP or PVC and an aluminium layer. Depending on the particular requirement, the film is made accordingly, e.g. to be more stable, if for example depressions are to be formed therein. The foil is also tear-resistant, for example by the incorporation of a PET layer, so that a medicament chamber can be opened by pulling the foil strip, without tearing.

In a preferred embodiment, the foil has an outer sealable layer which is on the inside relative to the blister. In this way, edge regions of pouches can be welded/fused by the application of heat.

It is also possible to use sealing lacquer, e.g. heat-sealing lacquer. This requires an additional step of applying the lacquer. As a result, there are more or other possible materials or material combinations for the foil or foil layers.

For sealing, heat is applied to the corresponding points which are to be welded or sealed. This can be done by various methods, e.g. by heat punches or by induction, while an aluminium layer may serve as the induction layer and the releases heat to the surrounding plastics layer, which is constructed as a separate lacquer coating, as an integrated layer of lacquer film or as a film coating.

The invention is hereinafter explained in more detail by means of examples and Figures described below.

DETAILED DESCRIPTION OF THE INVENTION

Figure 1:
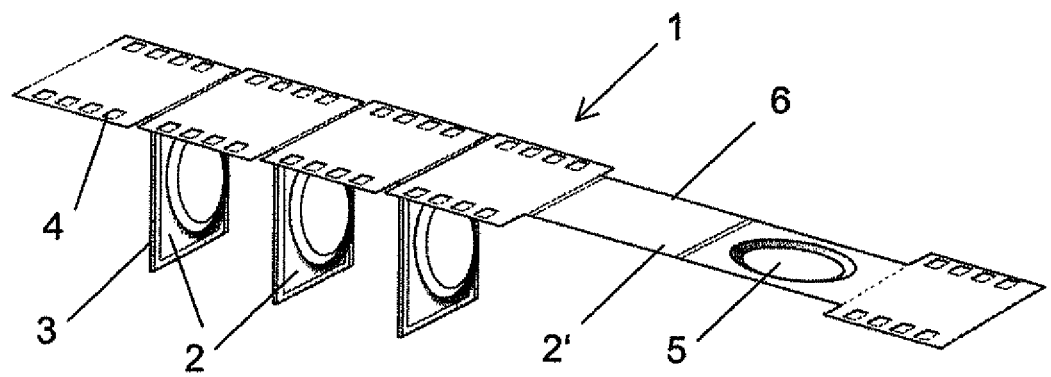
FIG. 1 a single-foil folded blister

FIG. 1 shows a folded blister 1 which is made from a single foil band. Pouches 2 are formed at regular intervals in the foil band, preferably containing a powdered medicament. To prevent medicament from escaping from the pouches they are sealed at their edges (seal 3). An opened medicament pouch 2' has a well-shaped depression 5 in the foil band on one side of the pouch, while the other side is a substantially planar cover. This type of foil configuration enables filling of the pouches in which essentially only the cover has to be moved, i.e. applied and removed, and for example a powder is contained in the depression without any risk of falling out, even during or after the opening of a pouch.

The pouches are arranged parallel to one another and at right angles to the longitudinal axis of the strip, the blister typically being transported in the direction along the longitudinal axis of the strip. This arrangement of the pouches behind one another enables the packing density to be kept very high.

The region 6 of the foil strip that forms a pouch is narrower than the rest of the foil strip. Openings 4 are provided in the wider parts of the foil strip that protrude laterally relative to the pouches. These openings serve for the engagement of transporting or openings pins of a corresponding transporting and/or opening means, e.g. a wheel.

The openings are located only between the individual pouches. The openings are arranged such that they form a substantially continuous row of openings after the formation of a pouch. However, it is also possible to distinguish between the individual pouches by means of different spacings, different sizes of openings, recesses, etc. (indexing). For example, a number of openings of the same size may be provided for transporting the blister, but only one single larger opening for each medicament pouch. A broad pin provided for stopping, for example, can correspondingly engage only in this larger opening and thereby initiate the stopping action.

Because of the special configuration of the blister it is possible to provide a single lateral opening for each pouch and to arrange adjacent pouches directly adjoining one another, apart from the gap for this lateral opening.

Owing to the fact that the pouch regions are narrower, the film blister may be guided laterally. The entire handling of the foil blister is essentially independent of the position and lie of the individual pouches. In particular, one or more transporting pins of one or more transporting wheels may engage laterally in the blister at any desired position or at any desired time. The pin or pins or wheels may be arranged parallel to the medicament magazine viewed in the direction of travel. The pins may be guided parallel and adjacent to the pouch. For the engagement of the pin or pins, there is no need to match up an accurate position between pouches. Nor is there any need to align a pouch above a sprocket wheel. The pouches may be superimposed in the manner of scales in a space-saving arrangement without affecting the transporting of the band. This independence is also particularly advantageous for a transition, e.g. from a transporting wheel to an opening wheel: the two may essentially be directly adjacent to one another. The pouches are located next to a wheel or in a space between two parallel wheels: such a space is in any case usually present because of the diameter of a wheel of this kind. Transporting and opening mechanisms can thus be arranged close together. The total width of the medicament magazine including transporting and opening means can thus be restricted to the width of the foil, without having to abandon a high pouch density and without giving rise to further disadvantages such as, for example, the gripping of multiple pouches by the transporting pins. The arrangement also confers advantages in terms of a medicament dispensing device in which a foil blister of this kind is installed. This may be designed largely independently of the depth of a pouch or the spacing thereof, particularly when an opening mechanism is triggered by the arrangement and/or configuration of the lateral openings.

Figure 2A:
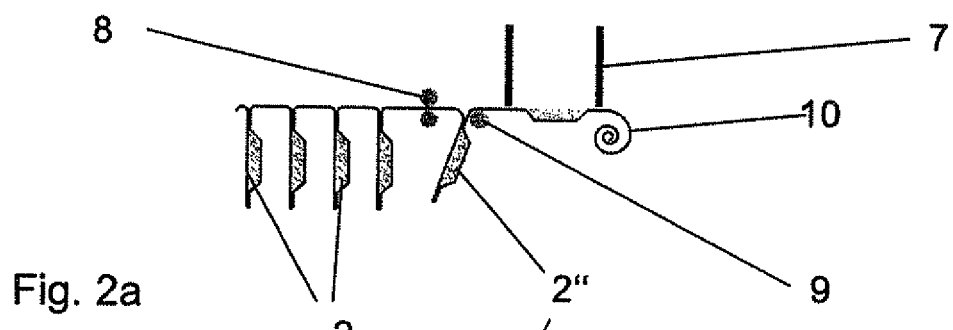
FIG. 2 the sequence of the opening operation of a single-foil folded blister
Figure 2B:
Figure 2C:

FIGS. 2a-c diagrammatically show the sequence of the process of opening a folded blister. In FIG. 2a a folded blister with a plurality of pouches 2 filled with a medicament is shown, with a front pouch 2" which is to be opened next, and with an opened pouch. The opened pouch is in a removal position, which is diagrammatically indicated by an inhalation chamber 7.

The blister is guided between two transporting wheels 8, an upper and a lower one. These may be fitted with a locking mechanism to secure the blister at a desired position, i.e. after moving through the medicament pouch 2". It is also possible to provide only a lower or upper transport wheel 8, with one transporting wheel preferably being arranged on both longitudinal sides of the blister strip. The blister or the medicament pouch to be opened is preferably stopped precisely at a point such that after opening it comes to lie directly in a removal position. While the transporting wheels are arranged behind a pouch, in relation to a direction of travel of the blister, one opening wheel 9 is arranged in front of the pouch which is to be opened, again viewed in the direction of travel. By means of the opening wheel, which preferably also engages with its pins in the openings of the blister and is arranged on both sides of the blister, the foil band can be pulled onwards at the front end and the pouch 2" can be opened. The opening wheel, which may be a sprocket wheel, is thus rotated by the distance needed to open the pouch. Because the opening wheel or wheels are also arranged laterally of the medicament pouch, a depression filled with medicament can be pulled past between the two laterally arranged opening wheels. The opening wheels also act as a guide.

The opening wheel may essentially be constructed as a transporting element and be moved by a corresponding distance together with and parallel to a front part of the foil strip in the direction of travel and thereby open a pouch. Preferably, the transportation into the opening position and the opening are carried out in individual steps one after another.

The tensile force for opening the pouches preferably comes from the opening wheel, but may also come from a winding reel 10 onto which the used, opened foil band is rolled up. A winding reel 10 would be provided with a corresponding slippage in order to be able to compensate for differences in diameter. If a tensile force comes from an opening wheel, the used foil band may for example also simply go into a space provided for it in a dispensing device or may emerge from this space, at which point the strip can be cut and removed.

Opening may essentially also be carried out by means of a winding reel without a separate opening wheel. Here, too, the winding reel preferably has some slippage.

In FIGS. 2b and 2c the pouch 2' which is to be opened is shown at various stages of transportation and opening. The transporting and opening wheels 8, 9 are designed as guides for a pouch provided with a depression and cover. As a result of the supporting function of the opening wheel the depression is brought into a horizontal position and held there. These measures prevent powder from escaping from a pouch during opening, e.g. as the result of a tilting of the foil blister or any force pulses that may occur during opening or transportation.

In a preferred embodiment a segmented wheel takes over the transporting and opening of the foil blister according to the invention, as is shown in more detail hereinafter in FIGS. 4 and 5a-d.

In a preferred embodiment, at least the portion of the foil strip with the medicament pouch which is to be opened is in the same plane as the opened medicament chamber in which the direction of the transporting and opening movement also lies.

If a medicament magazine of this kind is guided by two sprocket wheels arranged parallel, the pouches provided in the magazine are substantially freely movable in the region between the sprocket wheels. The depth of the pouches is optionally also restricted by a spindle that guides the two sprocket wheels. If it is desired to have deeper pouches or small sprocket wheels, the latter may, for example, be mounted from an outer side, so that the entire space between the wheels is free for the pouches, as is preferably also the case with single-foil folded blisters that are guided or transported only on one side.

Figure 3:
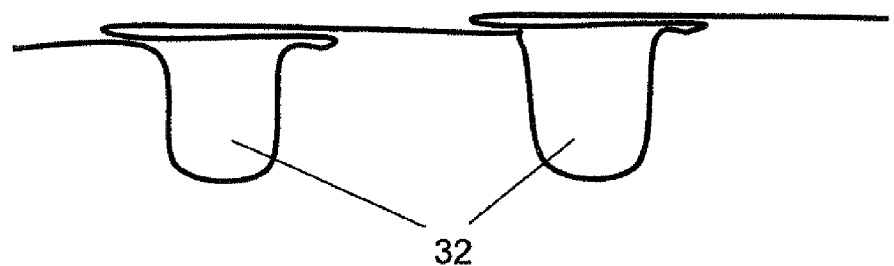
FIG. 3 another embodiment of a single-foil folded blister
Figure 4:
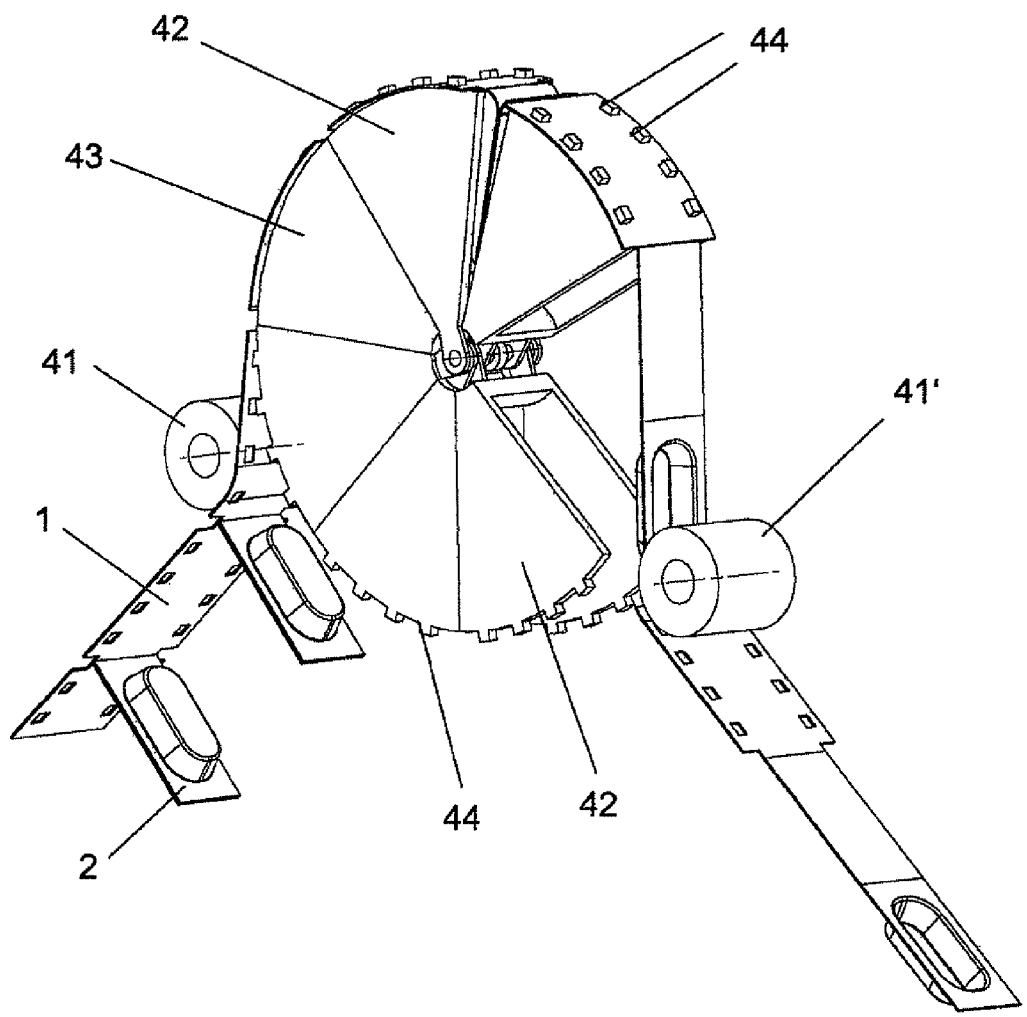
FIG. 4 a transporting and opening mechanism in the form of a segmented wheel

FIG. 3 shows another configuration or method of producing a single-foil folded blister. A pouch 32 is formed with a foil band. The pouch is laterally sealed (not shown in the Figure), a medicament is introduced and the foil is placed over the fill opening of the pouch, where it is also sealed on, thereby closing off the pouch. Narrower pouch regions and lateral openings in the blister do not have to be formed in the foil band beforehand, but may, for example, be provided at the same time as lateral sealing or upper sealing of the pouches is carried out.

Generally, a single-foil folded blister is made from only one foil strip. A pouch or a depression with its associated cover is made from one and the same foil and from successive foil portions.

FIG. 4, and FIG. 5a-d show a segmented wheel and an associated opening process for a folded blister according to the invention.

The foil blister 1 is in turn made from a foil band in which a plurality of medicament pouches 2 are formed. The foil band has a plurality of openings arranged regularly behind one another in the lateral edge regions of the foil band between the pouches. The foil regions that form the pouches are narrower and have no openings for transporting pins. The length of the regions between the pouches corresponds with the length of an arcuate segment of the circumference of the segmented wheel 43, this arcuate segment being formed by an end face of an individual segment 42. The shape and number of the openings provided in the foil band correspond with projections which serve as transporting pins, in this case four projections in each case, arranged in two rows. The projections are located on two sides of the segment arranged parallel to one another and face radially outwards. The folded blister is rolled up and unrolled again over the interlocking openings and transporting pins over part of the segmented wheel.

The individual segments have a U-shaped cross-section such that a medicament pouch comes to rest in the cavity between the segment sides. The segment sides, and hence the rows of transporting pins or individual transporting pins, are spaced from one another by at least one pouch width. Preferably they are only a little more, e.g. 0.1-2 mm, than one pouch width apart from one another, in order to allow transporting of a blister with as little friction as possible, so as to provide good guidance and take up as little space as possible. The segmented wheel is formed from a plurality of individually movable segments, in this case six segments, while all the segments together do not make up a complete circle. The free wheel region formed between two segments is used to open a medicament pouch, when an individual segment passes over it. It is accordingly matched to the length or twice the length of a medicament pouch. The blister strip and segments are matched to one another such that a medicament pouch comes to lie precisely between two segments. By separating the two segments from one another, the section of foil that forms a medicament pouch is pulled apart and exposes the medicament chamber and the medicament contained therein.

Immediately before and after the segmented wheel, two retaining rollers 41, 41' are provided, which hold the folded blister in position above and on the segmented wheel.

Figure 5A:
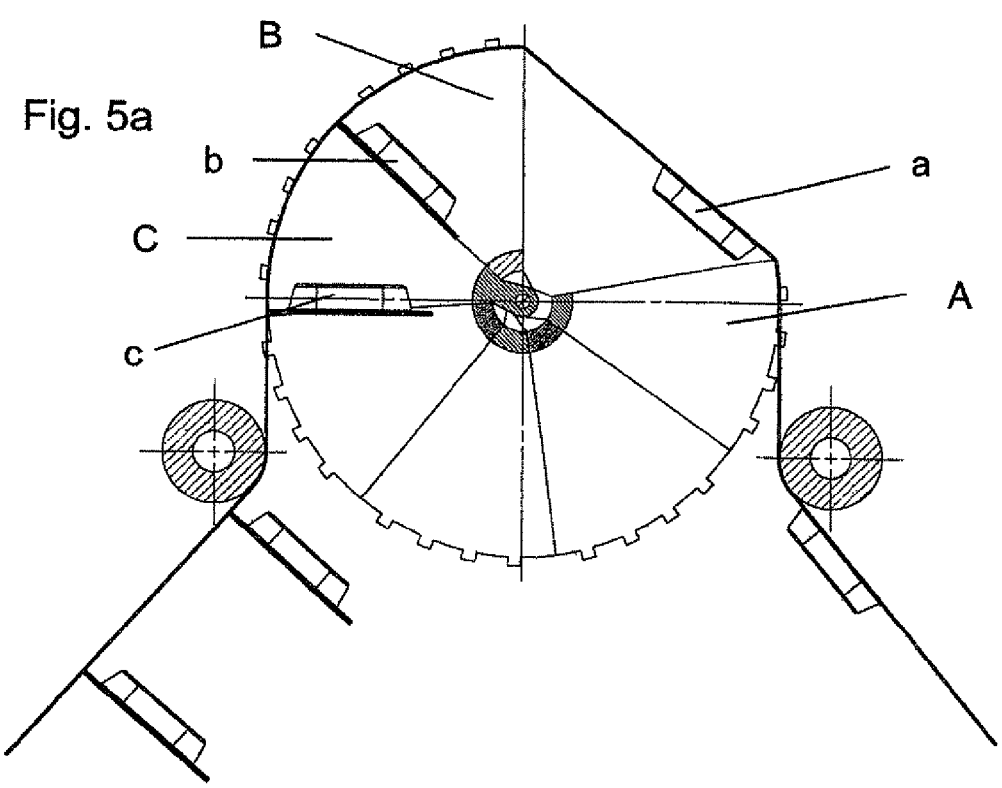
FIG. 5a-d various opening positions of a folded blister

An opening operation by means of the segmented wheel can be carried out as shown in FIGS. 5a-d. The folded blister is guided over the segmented wheel, while the transporting pins of the individual segments engage in the openings in the blister. Rotary movement of the wheel causes the blister to be transported with the wheel. FIG. 5a shows the blister in a removal position with an emptied medicament chamber. The removal position is in a segment-free region, all the segments being transported onwards abutting on one another.

Figure 5B:
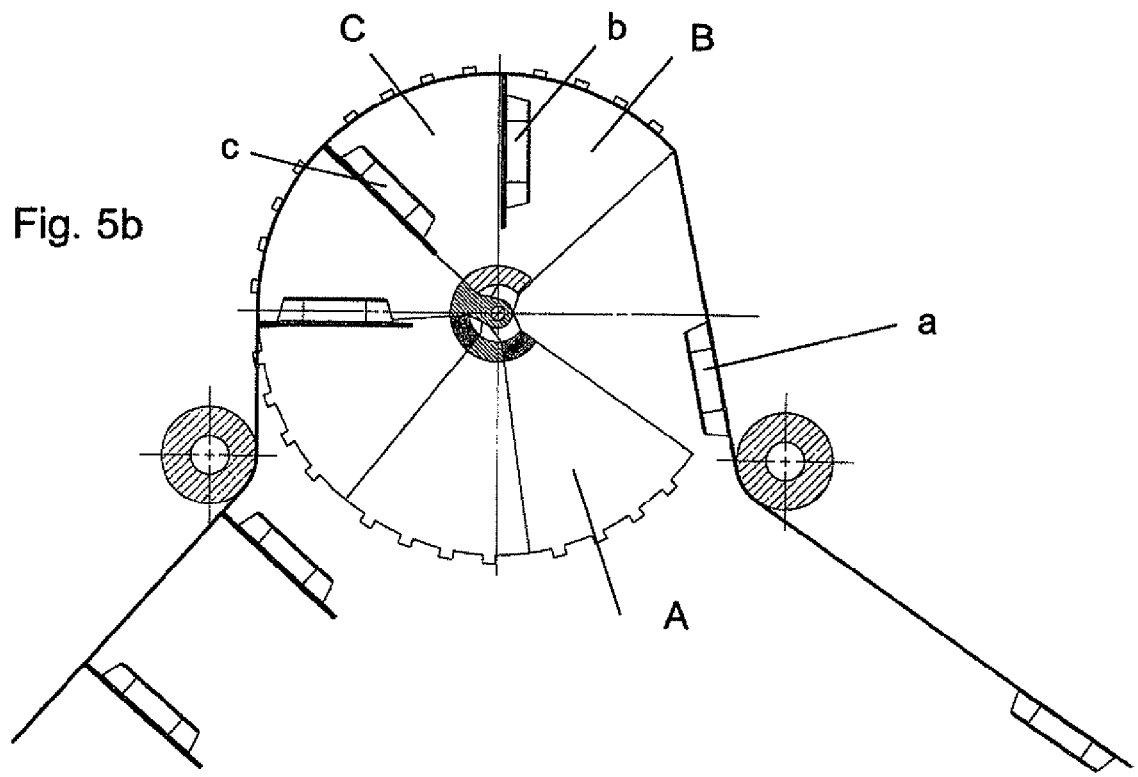
Figure 5C:
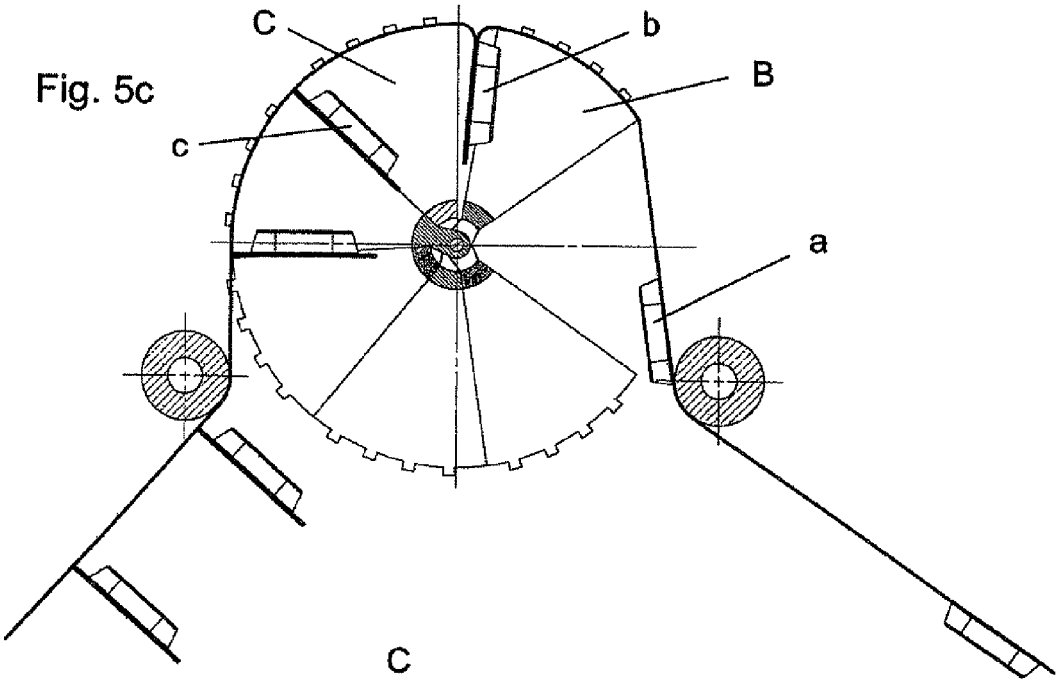
Figure 5D:
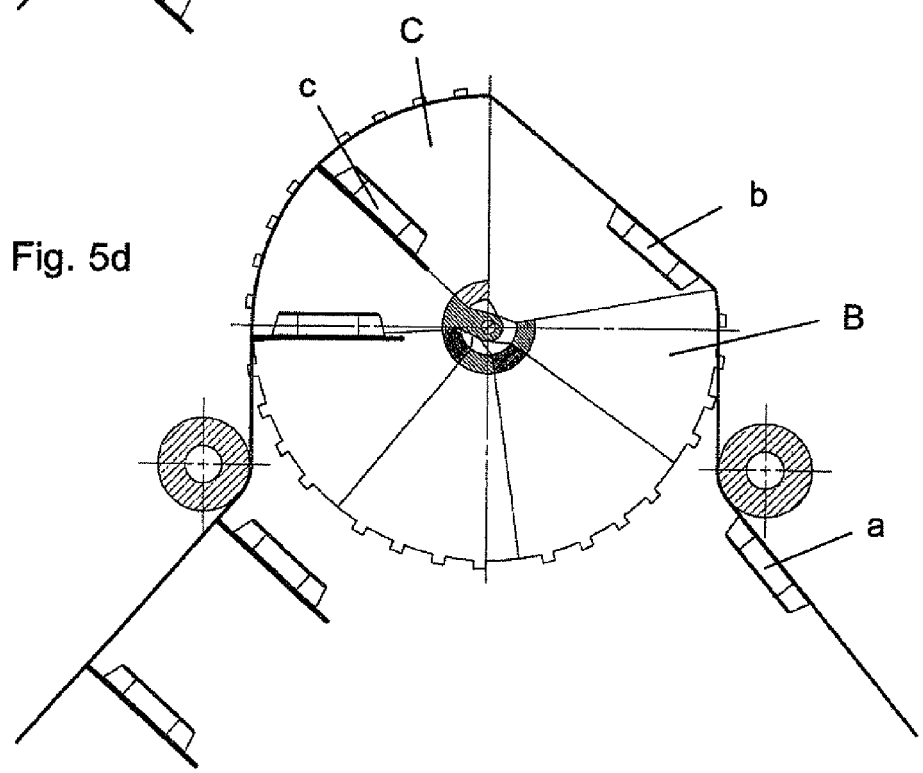

The rotary movement of the segmented wheel is continued until the next medicament pouch b is in an opening position, as shown in FIG. 5b. At this point a locking mechanism is triggered via a mechanism, e.g. in the hub of the segmented wheel, such that the blister strip is stopped at the opening position. Only the next segment B, which is followed directly by the next medicament pouch b to be opened, is moved onwards in the direction of travel (FIG. 5c). As a result of the force exerted on the foil band, the pouch b opens and comes to rest in the removal position, open and ready to be emptied, as shown in FIG. 5d. The projections of segment B hold the foil at segment B, while the projections on segment C hold the foil on segment C. The movement of segment B onwards in the direction of travel pulls the foil until the seals between the foil regions of the medicament are pulled apart and the pouch opens.

The next segment B is now adjacent to the other segments of the wheel which have been stationary up to this point and the process according to FIG. 5a-d can be repeated with the next-but-one medicament chamber c and the next-but-one segment C. During the opening process the used chamber a is moved away over the retaining roller 41', e.g. rolled onto a winding reel or discharged from a medicament device, where the piece of foil containing the used chamber can be removed.

The transporting of the segmented wheel, including the opening mechanism of a medicament pouch, can be combined with an opening mechanism of a medicament dispensing device, e.g. the opening of a mouthpiece of a multi-dose powder inhaler.

The segmented wheel and the two retaining rollers are fixed in position and are rotatable about their respective rotation axes in a medicament dispensing device such as an inhaler, for example.

The invention claimed is:

1. A magazine for a plurality of doses of a medicament, the magazine comprising a single foil strip in which pouches for holding the medicament are formed, the foil strip comprising longitudinal sides and openings on at least one of the longitudinal sides for transporting the pouches and for engagement with transporting pins, wherein the foil strip has a first width in regions of the pouches which is less than a second width of the foil strip in other regions, and the openings are located in the other regions of the foil strip.

2. The magazine according to claim 1, wherein the regions of the pouches have a width that is narrower than the other regions of the foil strip and the openings are provided in the other regions of the foil strip that protrude laterally relative to the pouches, the first and second foil widths differing by about a width of the openings.

3. The magazine according to claim 1, wherein the openings are located only in the other regions of the foil strip.

4. The magazine according to claim 1, wherein the openings in the foil strip for the engagement of transporting pins can also be used for opening the pouches.

5. The magazine according to claim 1, wherein the openings of the foil strip serve for the engagement of at least one of a transporting means and an opening means, and are located on both longitudinal sides of the foil strip.

6. The magazine according to claim 1, wherein the openings are elongated and have different lengths depending on their function.

7. The magazine according to claim 1, wherein the pouches are formed by depressions in the foil strip and a substantially planar cover.

8. A device for opening a magazine for a plurality of doses of a medicament comprising:
   a single foil strip in which pouches for holding the medicament are formed, the foil strip comprising longitudinal sides and openings on at least one of the longitudinal sides for transporting the pouches and for engagement with at least one movable transporting pin, wherein the foil strip has a first width in regions of the pouches which is less than a second width of the foil strip in other regions, and the openings are located in the other regions of the foil strip;
   the at least one movable transporting pin for engaging in at least one of the openings in the foil strip, and
   transporting means for the magazine and opening means for the magazine in order to open one of the pouches formed in the foil strip,
   wherein the at least one movable transporting pin is arranged such that it engages in the at least one of the openings in the foil strip parallel and laterally with respect to a transporting direction and at a spacing from one of the pouches.

9. The device according to claim 8, wherein the at least one movable transporting pin is part of a sprocket wheel.

10. The device according to claim 8, wherein the at least one movable transporting pin is arranged so that the one of the pouches is freely movable when in an area beside the at least one movable transporting pin.

11. The device according to claim 8, wherein at least two of the at least one movable transporting pin are arranged parallel to one another and spaced from one another by at least one pouch width.

12. The device according to claim 8, wherein the transporting means for the magazine and the opening means for the magazine are combined in a discontinuous pin wheel.

13. The device according to claim 12, wherein the pin wheel is constructed as a segmented wheel having a plurality of segments, and a maximum spacing between two sequential segments corresponding to about a length of an opened medicament pouch.

14. A method of transporting and opening a magazine comprising a single foil strip in which pouches for holding the medicament are formed, the foil strip comprising longitudinal sides and openings on at least one of the longitudinal sides for transporting the pouches and for engagement with transporting pins, wherein the foil strip has a first width in regions of the pouches which is less than a second width of the foil strip in other regions, and the openings are located in the other regions of the foil strip, the method comprising the steps of:
(i) engaging at least one transporting pin of a pin wheel in at least one of the openings in the magazine;
(ii) transporting the pouches by rotation of the pin wheel into a region of an opening position whereby a portion of the magazine is held in front of at least one of the pouches in the region of the opening position; and
(iii) opening the at least one of the pouches by means of the at least one transporting pin, whereby the medicament contained in the at least one of the pouches is exposed.

15. The method according to claim 14, wherein the at least one of the pouches is opened by at least two transporting pins engaging the openings in the magazine and moving the pouches away relative to one another.

16. The method according to claim 14, wherein the at least one of pouches is configured to be arranged between two segments of a segmented wheel and is opened by moving the two segments apart.

17. A multi-dose powder inhaler comprising a magazine for a medicament, comprising a single foil strip in which pouches for holding the medicament are formed, the foil strip comprising longitudinal sides and openings on at least one of the longitudinal sides for transporting the pouches and for engagement with transporting pins, wherein the foil strip has a first width in regions of the pouches which is less than a second width of the foil strip in other regions, and the openings are located in the other regions of the foil strip.

18. The multi-dose Multi dose powder inhaler according to claim 17 comprising 60 single doses of medicament.

19. The multi-dose powder inhaler according to claim 17 wherein the medicament contains an active substance or a combination of active substances selected from among the betamimetics, anticholinergics, steroids, antiallergics, ergot alkaloid derivatives, triptanes, CGRP antagonists, the phosphodiesterase-V inhibitors, phosphodiesterase-IV inhibitors, LTD4-antagonists, and EGFR-kinase inhibitors.

* * * * *